United States Patent [19]

Yamasaki

[11] Patent Number: 5,116,733
[45] Date of Patent: * May 26, 1992

[54] METHOD OF ASSAYING TARGET SUBSTANCE

[75] Inventor: Masahiko Yamasaki, Tokyo, Japan

[73] Assignee: Konica Corporation, Tokyo, Japan

[*] Notice: The portion of the term of this patent subsequent to May 1, 2007 has been disclaimed.

[21] Appl. No.: 396,681

[22] Filed: Aug. 22, 1989

[30] Foreign Application Priority Data

Aug. 22, 1988 [JP] Japan .................. 63-208749

[51] Int. Cl.$^5$ .................. C12Q 1/78; C12Q 1/68; C12Q 1/00; G01N 33/53
[52] U.S. Cl. .................. 435/28; 435/4; 435/7.9; 435/174; 435/181; 435/180; 435/6; 436/501; 436/524
[58] Field of Search .................. 435/28, 181, 180, 4, 435/7.9, 174, 6; 436/501, 524

[56] References Cited

U.S. PATENT DOCUMENTS

| | | | |
|---|---|---|---|
| 4,247,631 | 1/1981 | Nix et al. .................. | 435/10 |
| 4,295,853 | 10/1981 | Kasaham et al. .................. | 23/230 B |
| 4,672,029 | 6/1987 | Washburn et al. .................. | 435/10 |
| 4,727,024 | 2/1988 | Koocher et al. .................. | 435/7.4 |
| 4,885,250 | 12/1989 | Eveleigh et al. .................. | 435/181 |
| 4,921,791 | 5/1990 | Yamasaki et al. .................. | 435/28 |

OTHER PUBLICATIONS

White (1986) Medical Virology Academic Press, Orlando, p. 330.

*Primary Examiner*—Christine Nucker
*Assistant Examiner*—David R. Preston
*Attorney, Agent, or Firm*—Finnegan, Henderson, Farabow, Garrett & Dunner

[57] ABSTRACT

Disclosed is a method of assaying a target substance. In the method of the present invention, a complex of the target substance and a substance labelled with peroxidase is fixed to a hydrophobic membrane. Then hydrogen peroxide, an aromatic primary amine and a phenolic compound are contacted with the peroxidase on the membrane to generate and deposit color on the hydrophobic membrane. The deposited color is then measured so as to assay the target substance.

1 Claim, No Drawings

METHOD OF ASSAYING TARGET SUBSTANCE

BACKGROUND OF THE INVENTION

I. Field of the Invention

This invention relates to a method of assaying a target substance.

II. Description of the Related Art

Various methods for assaying a target substance such as a biological substance have been developed. Among these, the most sensitive methods are those utilizing the specific binding reaction between a target substance and a substance which specifically reacts with the target substance (hereinafter referred to as "specifically binding substance" for short), for example, specific binding reaction between an antigen and an antibody, a sugar chain and lectin, biotin and avidin, Protein A and IgG, a hormone and a receptor, or an enzyme and a substrate.

In general, the specific binding substance labelled with a marker (hereinafter referred to as "labelled substance" for short) is utilized, and the signal from the labelled substance, which varies depending on the amount of the target substance to be assayed, is measured so as to assay the target substance.

In particular, in a conventional method, a target substance directly or indirectly fixed to a support is reacted with the labelled substance to fix the complex therebetween on the support, and the signal from the labelled substance on the support, which varies depending on the amount of the target substance to be assayed, is measured so as to assay the target substance.

Examples of this type of methods include an assay in which a protein component (target substance) separated by electrophoresis is transferred to a nitrocellulose membrane from the electrophoresis gel, and a labelled substance (e.g., a labelled antibody) is then reacted with the protein on the nitrocellulose membrane, followed by measuring the signal from the labelled substance; an assay in which a target substance on a thin layer chromatography (TLC) plate, such as a lipid fractionated by TLC is reacted with a labelled substance and the signal from the labelled substance is measured; an assay in which a DNA and a labelled DNA complementary to the DNA are reacted to detect a signal from the labelled substance; and immunohistochemical staining methods.

By these assays, not only the quantification of the target substance or the reactivity between the target substance and the specifically binding substance, but also much information about the property and/or the state of existence of the target substance and/or the specifically binding substance may be obtained. For example, by the assay in which a biological target substance such as a protein or a nucleic acid transferred to a nitrocellulose membrane from the gel after electrophoresis, or a lipid fractionated on a TLC plate is reacted with a labelled substance and the signal from the labelled substance is measured, the location of the target substance may be determined, and the molecular weight, isoelectric point and/or the polarity of the target substance may be determined from the mobility of the target substance.

By the immunohistochemical staining method, information such as the location and/or the state of existence of the target substance in a tissue may be obtained.

In the above-mentioned assay in which the target substance directly or indirectly fixed on a support is assayed by measuring the signal from the complex between the target substance and the labelled substance, since the amount of the target substance is very small, it is required that the marker be detected with high sensitivity, and in order to obtain more information about the target substance, it is required that the marker be detected with high resolution.

To satisfy these requirements, radioactive isotopes, fluorescent substances, luminescent substances and enzymes are conventionally utilized as the marker.

When a radioactive substance is utilized, however, the radioactivity of the marker is decreased with time, discarding the radioactive marker is troublesome and there is a danger for an operator to be exposed to the radioactivity. Further, the equipment is expensive. Still further, when the signal from the marker fixed on the support is measured, time consuming and troublesome operations such as exposure of photographic material and development thereof are needed.

Similarly, when a fluorescent or luminescent marker is employed, a special equipment is required.

On the other hand, in cases where an enzyme is employed as a marker, the operation is relatively simple, the generated color can easily be visualized and the quantification of the color can easily be attained. As the labelling enzyme, peroxidase, alkaline phosphatase and β-galactosidase are conventionally employed. In the assay in which a pigment is formed by an enzyme reaction on the support on which the complex is fixed, peroxidase is mainly used as the labelling enzyme and diaminobenzidine, o-dianizidine or 4-chloro-1-naphthol is conventionally used as the substrate.

Diaminobenzidine and o-dianizidine, however, have a drawback in that they have strong toxicity and they give high background. 4-chloro-1-naphthol has unsatisfactory sensitivity in view of obtaining more information about the target substance, although it gives higher sensitivity than the other two substrates.

The present inventors have developed a method of assaying a target substance with high sensitivity and high resolution, which can be carried out quickly, and the method is disclosed in Japanese Patent Disclosure (Kokai) No. 150723/86. In this method, a complex between a target substance to be assayed and a labelled substance labelled with peroxidase is fixed on a support, a pigment is formed by the enzyme reaction of the peroxidase and the pigment is deposited on the substrate, wherein hydrogen peroxide, an aromatic primary amine and a phenolic compound are used as the substrate.

The support employed in this type of method is usually in the form of a membrane and nitrocellulose membrane which is hydrophilic is most widely used as the support.

However, in the above-described sensitive method wherein hydrogen peroxide, an aromatic primary amine and a phenolic compound are used as the substrates, if a nitrocellulose membrane is used as the support, the pigment formed and deposited on the nitrocellulose membane is decomposed with time, especially by the action of light. The decomposition of the pigment is a serious problem on the accuracy of the assay and on the long time storage of the record.

SUMMARY OF THE INVENTION

Accordingly, the object of the present invention is to provide a method of assaying a target substance with high sensitivity in which the decomposition of the pigment formed by the enzyme reaction by the marker enzyme is inhibited.

The present inventors have intensively studied to find that the above-mentioned object may be accomplished by employing peroxidase as the marker enzyme, hydrogen peroxide, an aromatic primary amine compound and a phenolic compound as the substrates and a hydrophobic support as the support, to complete the present invention.

That is, the present invention provides a method of assaying a target substance comprising the steps of fixing on a hydrophobic membrane a complex of the target substance to be assayed and a labelled substance which specifically reacts with the target substance, said labelled substance being labelled with peroxidase; contacting hydrogen peroxide, an aromatic primary amine compound and a phenolic compound with the peroxidase on the membrane to generate and deposite color on the hydrophobic membrane; and measuring the color deposited on the hydrophobic membrane.

By the method of the present invention, the target substance may be assayed with high sensitivity and high resolution. Further, the pigment formed by the enzyme reaction by the peroxidase and deposited on the hydrophobic support is substantially not decomposed with time. Therefore, the results of the assay are accurate and the raw data of the assay can be stored for a long time.

DETAILED DESCRIPTION OF THE PREFERRED EMBODIMENTS

As mentioned above, the support employed in the method of the present invention is a hydrophobic membrane. The hydrophobic membrane is a membrane substantialy made of a hydrophobic macromolecular substance. The hydrophobic macromolecular substance is a material which substantially does not have an affinity to water and have a property of not absorbing water. The hydrophobic material forming the hydrophobic membrane preferably has a water-absorption determined according to ASTM D 570 of not more than 0.5%, more preferably not more than 0.1%.

Preferred examples of the hydrophobic macromolecular materials may include polyethylenes, polypropylenes, polyacetals, polystyrenes, epoxy resins, polycarbonates, fluorine-contained polymers and polyvinylidene chlorides. Among these, most preferred are fluorine-contained polymers, especially polyfluorovinylidenes.

Water absorptions of the popular polymers determined according to ASTM D 570 are summarized below (copied from "Handbook for Highpolymer Materials", Highpolymer Associate eds., published by Corona Co., Ltd., Japan, pp.1291-1293, 1973).

| Highpolymer Materials | Water Absorption (%) |
|---|---|
| [Hydrophobic Materials] | |
| Polyethylene | <0.01 |
| Polypropylene | <0.03 |
| Polyacetal | 0.2-0.29 |
| Polystyrene | <0.03-0.10 |
| Epoxy Resin | 0.08-0.15 |
| Polycarbonate | 0.15-0.18 |
| Fluorine-contained Resin | 0.00-0.04 |
| Polyvinylidene Chloride | 0.1 |
| Polyfluorovinylidene | 0.04 |
| [Hydrophilic Materials] | |
| Nitrocellulose | 1.0-2.0 |
| Nylon 66 | 1.1-1.5 |
| Nylon 6 | 1.3-1.9 |

Since the hydrophobic membrane has poor affinity to water and repulses water, in some cases, wetting operation of the hydrophobic membrane may be required when it is used for making the membrane affinitive to water before use. The wetting operation may be accomplished by sufficiently immersing the hydrophobic membrane in an organic solvent which is miscible with water and then immersing the resulting membrane in water or in a buffer to be used.

Fixing of a substance such as the target substance, specifically binding substance or the complex may be carried out by contacting the substance with the membrane which has been made affinitive to water.

In the method of the present invention, the target substance may be directly fixed on the membrane by physical adsorption or by chemical binding such as covalent bond, or may be indirectly fixed on the support via one or more other specifically binding substances. The target substance may be first fixed on the membrane and then the labelled substance may be reacted with the target substance to form the complex therebetween. Alternatively, after a complex of the target substance and the labelled substance is formed, the complex may be fixed on the support. Further, the labelled substance may be directly bound to the target substance or may be indirectly bound to the target substance via one or more other specifically binding substances.

In the method of the labelled substance, the labelled substance which is labelled with peroxidase may also be labelled with an anti-peroxidase antibody.

As the substrate of the enzyme reaction of the peroxidase, hydrogen peroxide, an aromatic primary amine compound and a phenolic compound are employed. The aromatic primary amine compound is oxidized by the action of the peroxidase and hydrogen peroxide, and the oxidized aromatic primary amine compound is then coupled with the phenolic compound to form and deposit a pigment.

In the method of the present invention, the target substance may be any substance for which a substance which specifically binds thereto can be obtained. Examples of the target substance include proteins, nucleic acids, hormones, lipids, complex carbohydrates, glycolipids, polysaccharides, enzymes, vitamines, antigens and antibodies.

The specifically binding substance is a substance which specifically binds to the target substance or to another specifically binding substance which specifically binds to the target substance. The specifically binding substance may appropriately be selected depending on the target substance. Examples of the specifically binding substance may include proteins, nucleic acids, hormones, lipids, complex carbohydrates, glycolipids, polysaccharides, enzymes, vitamines, antigens, antibodies, lectins, Protein A, avidin, biotin, receptors, co-enzymes, substrates of enzymes, toxins and complements as well as complexes thereof.

In the method of the present invention, preferred examples of the aromatic primary amine compound may include o- or p-aminophenolic compounds and p-phenylenediamine compounds as well as salts thereof.

The most preferred aromatic primary amine compound in the method of the present invention is p-phenylenediamine compound of the formula [I].

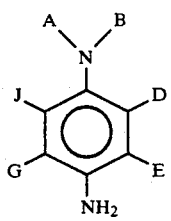

wherein A and B independently represent hydrogen or alkyl, or A and B cooperatively form a heterocyclic ring with the nitrogen; D, E, G and J independently represent hydrogen, halogen, hydroxy, amino, alkoxy, acylamide, arylsulfonamide, alkylsulfonamide or alkyl.

As the alkyl group represented by A or B, $C_1$-$C_6$ alkyl groups, especially $C_1$-$C_4$ alkyl groups are preferred. Examples of such alkyl groups include methyl, ethyl and butyl groups. The alkyl groups may have one or more substituents. Examples of the substituents may include hydroxyl, ureido, tetrahydrofuryl, carboxyl, methanesulfonamide, sulfo, methoxy, ethoxy, methoxyethoxy, methoxyethoxyethoxy and methoxytetraethoxy groups. Among these, especially preferred are hydroxyl and methansulfonamide groups.

Preferred examples of D, G and J may include hydrogen, alkoxy, alkylsulfonamide and arylsulfonamide groups, and most preferred is hydrogen. Preferred examples of E may include hydrogen, alkyl, and acylamide groups and most preferred are $C_1$-$C_3$ alkyl groups, especially methyl group.

Preferred examples of the salts of the aromatic primary amine compound of the formula [I] may include salts of organic and inorganic acids such as p-toluenesulfonic acid, sulfonic acid, sulfinic acid, sulfates, sulfamic acid, thiosulfuric acid S-esters, carboxylic acids, phosphates, amide phosphoric acid, phosphoric acid, phosphites, organic boron compounds, hydrochloric acid and sulfuric acid. Among these, the most preferred are p-toluenesulfonic acid salt, hydrochloric acid salt and sulfuric acid salt.

Preferred specific examples of the aromatic amine compound will now be enumerated. Needless to say, however, the aromatic amine compound is not limited thereto.

(1-1) N,N-diethyl-3-methyl-4-aminoaniline
(1-2) N,N-diethyl-4-aminoaniline
(1-3) N-carbamidemethyl-N-methyl-4-aminoaniline
(1-4) N-carbamidemethyl-N-tetrahydrofurfuryl-3-methyl-4-aminoaniline
(1-5) N-ethyl-N-carboxymethyl-3-methyl-4-aminoaniline
(1-6) N-carbamidemethyl-N-ethyl-3-methyl-4-aminoaniline
(1-7) N-ethyl-N-tetrahydrofurfuryl-3-methyl-4-aminophenol
(1-8) 3-acetylamino-4-aminodimethylaniline
(1-9) N-ethyl-N-β methanesulfonamideethyl-4-aminoaniline
(1-10) N-ethyl-N- β methanesulfonamideethyl-3-methyl-4-aminoaniline
(1-11) N-methyl-N-β sulfoethyl-p-phenylenediamine
(1-12) N-ethyl-N-hydroxyethyl-3-methyl-4-aminoaniline
(1-13) N-ethyl-N-[2-(2-methoxyethoxy)ethyl]-3-methyl-4-aminoaniline
(1-14) N-ethyl-N-{2-[2-(2-methoxyethoxy)ethoxy]ethyl}-3-methyl-4-aminoaniline
(1-15) N-ethyl-N-[2-{2-[2-(2-methoxyethoxyethoxy)ethoxy]ethoxy}ethyl]-3-methyl-4-aminoaniline
(1-16) N,N-diethyl-3-methanesulfonamideethyl-4-aminoaniline The salts of the compounds of the formula [I] are generally water-soluble, so that they can easily be soluted in water or buffer.

The phenolic compounds which may be employed in the method of the present invention are those which form a pigment by coupling with the oxidized aromatic primary amine compound. Preferably, the phenolic compound has a substituent on the benzene ring in order to decrease the solubility to water.

Preferred phenolic compounds are those of which 4-position is not substituted or substituted with a group or an atom which can be detached when the phenolic compound is subjected to the coupling reaction with the oxidized aromatic primary amine compound (the group or the atom is hereinafter referred to as "detaching group" or "detaching atom", respectively).

Preferred phenolic compounds may be represented by the formula [II].

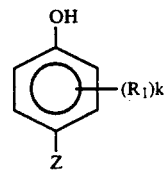

wherein $R_1$ represents a monovalent organic group or a monovalent atom, z represents hydrogen, detaching group or a detaching atom, k represents an integer of 1 to 4.

Preferred examples of the detaching atom represented by Z include halogen atoms such as chlorine and bromine.

Preferred examples of the detaching group represented by Z may include —$OR_2$, —$OCOR_2$, —$OSO_2R_2$, —$SR_2$, —$OCONHR_2$, —$OSO_2NHR_2$,

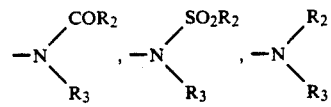

and —SCN. In these formulae, $R_2$ and $R_3$, the same or different, represent hydrogen, aliphatic carbohydrate residue, alicyclic residue, aryl group or heterocyclic residue.

Examples of the atom represented by $R_1$ include halogen atoms such as chlorine and bromine, preferably chlorine.

Examples of the monovalent organic group represented by $R_1$ may include aliphatic carbohydrate residue, alicyclic residue, heterocyclic residue, aryl group, —SCN, —$OR_4$, —$OCOR_4$, —$OSO_2R_4$, —$SR_4$, —$OCONHR_4$, —$OSO_2NHR_4$,

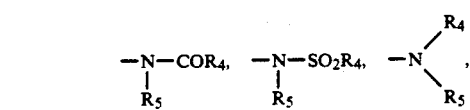

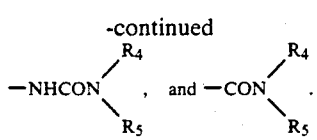

In these formulae, R4 and R5 independently represent hydrogen, aliphatic carbohydrate residue, alicyclic residue, aryl group or heterocyclic residue.

The aliphatic carbohydrate residue represented by $R_1$, $R_2$, $R_3$, $R_4$ or $R_5$ may be saturated or unsaturated and may be straight or branched. Preferred examples of the aliphatic carbohydrate residue may include alkyl groups (e.g., methyl, ethyl, propyl, isopropyl, butyl, t-butyl, isobutyl, dodecyl or octadecyl groups) and alkenyl groups (e.g., allyl or octenyl group).

Preferred examples of the alicyclic residue represented by $R_1$, $R_2$, $R_3$, $R_4$ or $R_5$ may include five-membered or six-membered alicyclic groups such as cyclopentyl group and cyclohexyl group.

Preferred examples of the heterocyclic residue represented by $R_1$, $R_2$, $R_3$, $R_4$ or $R_5$ may include pyridinyl, pyradinyl, pyridadinyl, quinolyl, pyrrolidyl, furaryl, thienyl, piperidyl, pyrrolyl, pyrronilyl, tetrazolyl, thiazonyl, imidazolyl, morpholyl, furyl, oxazolyl, thiazolyl, benzimidazolyl, benzoxazolyl and benzthiazolyl groups.

Preferred examples of the aryl groups represented by $R_1$, $R_2$, $R_3$, $R_4$ or $R_5$ includes phenyl group and naphthyl group.

The non-aromatic ring fused to the benzene ring, which is cooperatively formed by two $R_1$ may include five-membered and six-membered rings such as cyclopentane, cyclohexane and cyclohexene rings.

Preferred examples of the aromatic ring fused to the benzene ring, which is cooperatively formed by two $R_1$, especially the two $R_1$ at 5- and 6-position may include five-membered and 6-membered rings such as phenyl, pyridinyl, pyradinyl, pyridadinyl, pyrolidyl, furaryl, thienyl, pyperidyl, pyrrolyl, pyrrolinyl, thiadinyl, imidazolyl, furyl, oxazolyl and thiazolyl groups.

The aliphatic carbohydrate residue, alicyclic residue, aryl groups and the heterocyclic residue, as well as the non-aromatic ring and the aromatic ring fused to the benzene ring, which is cooperatively formed by the two $R_1$, may have one or more substituents.

Examples of the substituents may include halogen atoms (e.g., chlorine and bromine), nitro, cyano, hydroxy, keto, carboxyl, sulfo, amino (such as amino, alkylamino, dialkylamino, anilino and N-alkylanilino), alkyl (such as methyl, propyl, isopropyl, t-butyl, octadecyl, cyanoalkyl, haloalkyl and aralkyl), alkenyl, aryl groups (such as phenyl, tollyl, acetylaminophenyl, 4-lauroylaminophenyl and ethoxyphenyl), heterocyclic residue, alkoxy (such as ethoxy, phenoxy, methoxy and tetradecyloxy), aryloxy (such as phenoxy, 2,4-di-t-aminophenoxy, p-t-butylphenoxy, 4-dodecyloxyphenoxy, 4-hydroxy-3-butylphenoxy and 4-hydroxy-3-butylphenoxy), arylthio, amide (such as acetamide, methanesulfonamide and p-dodecylbenzenesulfonamide), carbamoyl (such as N-p-carboxymethoxyphenylcarbamoyl, N,N-dihexylcarbamoyl, N-benzylcarbamoyl, N-ethylcarbamoyl and N-ethoxyethylcarbamoyl), sulfamoyl (such as N,N-diethylsulfamoyl), alkylsulfonyl, arylsulfonyl (such as benzene sulfonyl and m-chlorobenzene sulfonyl) acyl (such as acetyl, p-chlorobenzoyl and benzoyl), acyloxy (such as acetyloxy and m-chlorobenzoyloxy), acyloxycarbonyl and alkoxycarbonyl (such as N-methoxyethylcarbamoylmethoxycarbonyl, ethoxycarbonyl, methoxycarbonyl and triethoxycarbonyl), aryloxycarbonyl (such as phenoxycarbonyl and p-nitrophenoxycarbonyl), arylthiocarbonyl (such as phenylthiocarbonyl) and imide groups (such as succinimide and octadecylsuccinimide).

Preferred specific examples of the phenolic compounds which may be employed in the method of the present invention will now be enumerated. Needless to say, the phenolic compounds are not limited thereto.
(2-1) 2-benzyl-4-chlorophenol
(2-2) N-benzoyl-4,6-dichloro-5-methyl-2-aminophenol
(2-3) 2-benzoylamino-5-acetamino-4-chlorophenol
(2-4) 4-chloro-1-naphthol
(2-5) 4-methoxy-1-naphthol
(2-6) 2,4-dichloro-1-naphthol
(2-7) 1-hydroxy-4-bromo-N-ethyl-2-naphthamide
(2-8) 1-hydroxy-4-methoxy-N-propyl-2-naphthamide
(2-9) 2,6-dibromo-1,5-dihydroxy-naphthalene
(2-10) 1-hydroxy-5-phenylsulfonamidenaphthol
(2-11) 1-hydroxy-2,4-dichlro-5-nitronaphthol
(2-12) 4-bromo-1-naphthol
(2-13) 4-ethoxy-1-naphthol
(2-14) 4-butoxy-1-naphthol
(2-15) 4-sulfo-1-naphthol
(2-16) 4-(2-methoxyethoxy)-1-naphthol
(2-17) 4-methylthio-1-naphthol
(2-18) 4-phenylthio-1-naphthol
(2-19) 4-phenylazo-1-naphthol
(2-20) 4,5-dimethoxy-1-naphthol
(2-21) 4-contasulfonamide-1-naphthol
(2-22) 4-(2-aminophenylazo)-2-propyl-1-naphthol
(2-23) 4,7-dimethoxy-2-methoxymethyl-1-naphthol
(2-24) 4-chloro-2-dimethylcarbamoyl-1-naphtol
(2-25) 4-(1-carboxybutoxy)-1-naphthol
(2-26) 4-chloro-2-acetylamino-1-naphthol The pigment may be formed and deposited on the complex of the target substance and peroxidase-labelled substance, which is fixed on the membrane by immersing the membrane in a coloring substrate solution. The coloring substrate solution may be prepared by dissolving hydrogen peroxide, the aromatic primary amine compound and phenolic compound in a buffer with an appropriate pH. The phenolic compound may be added to the solution after dissolving the phenolic compound in a hydrophilic organic solvent such as methanol, ethanol and dimethylformamide. The preferred molar ratio of the aromatic primary amine compound to the phenolic compound may be 1:100 to 100:1, more preferably 1:10 to 10:1.

After the pigment is sufficiently formed and deposited on the membrane by the enzyme reaction, the non-reacted substances are washed to stop the reaction.

The deposited pigment may be visually observed or may be measured by means of a conventional technique such as by measuring the absorbance or reflectance utilizing a spectrophotometer or the like.

The method of the present invention may be applied to any assay in which a complex of a target substance to be assayed and a labelled substance is, directly or indirectly, fixed to a support. For example, in one embodiment of the method of the present invention, a target substance such as a protein separated by electrophoresis is transferred to the hydrophobic membrane from the electrophoresis gel, and a labelled substance such as a labelled antibody is then reacted with the target substance on the hydrophobic membrane followed by the above-mentioned enzymatic coloring reaction and measurement of the color formed and deposited on the hydrophobic membrane. In still another embodiment of the present invention, a DNA and a labelled DNA complementary to the DNA are reacted on the hydrophobic membrane and the color formed by the enzymatic coloring reaction is measured. Still further, the method of the present invention may be applied to a qualititative or quantitative determination of a target substance contained in a fluid sample. This type of assay may be accomplished by, for example, utilizing the competitive reaction of the target substance contained in the fluid sample and the target substance preliminarily fixed to the hydrophobic membrane, with the peroxidase-labelled substance. It is apparent for those skilled in the art that the method of the present invention may be applied to many other types of assays.

The invention will now be described by way of examples thereof. It should be noted, however, the examples are presented for the illustration purpose only and should not be interpreted in any restrictive way.

EXAMPLE 1

Assay of Protein Antigen on Hydrophobic membrane

A hydrophobic membrane of polyvinylidene fluoride was immersed in methanol for 20 seconds and then in phosphate buffered physiological saline (pH 7.4) (hereinafter referred to as PBS for short) for 1 hour. For comparison, a nitrocellulose membrane was immersed in PBS for 5 minutes.

On the respective membrane, 40 μl of serially diluted monoclonal mouse IgM in PBS was dot-blotted as an antigen with a blotting apparatus (commercially available from Bio-Rad). The membranes carrying the antigen were blocked with 1% bovine serum albumin (BSA) in PBS at 4° C. overnight. Then the membranes were reacted with peroxidase-labelled goat anti-mouse IgM antibody (commercially available from Cappel, 200-fold diluted with 1% BSA-PBS) at room temperature for 2 hours. The membranes were then washed five times with 0.05% Tween-20 (polyoxyethylenesorbitan monolaurate, commercially available from Wako Pure Chemicals), and were immersed in a coloring substrate solution. The coloring substrate solution was prepared by adding 50 ml of 50 mM Tris-HCl containing 10 mg of N-ethyl-N-β methansulfonamideethyl-3-methyl-4-aminoaniline 3/2 sulfate.H₂O to 10 ml of methanol containing 30 mg of 4-chloro-1-naphthol and then adding 200 μl of hydrogen peroxide to the resulting mixture. Fifteen minutes later, the membranes were taken out of the coloring solution and were sufficiently washed with water to stop the coloring reaction.

After drying, the membranes were placed at 7 cm away from a fluorescent lamp with a power of 18 W and the reflection density at 650 nm of the colored spots and the background were measured at 0, 15 and 22 hours after the beginning of the irradiation with the fluorescent lamp. The reflection density of the background was also measured at 450 nm. The results are shown in the table below.

TABLE

| | Membrane | | | | | |
| --- | --- | --- | --- | --- | --- | --- |
| | Polyfluorovinylidene | | | nitrocellulose | | |
| | Time (hr) | | | | | |
| Antigen (ng) | 0 | 15 | 22 | 0 | 15 | 22 |
| 100 | 1.19 | 1.16 | 1.11 | 0.65 | 0.50 | 0.18 |
| 20 | 1.04 | 1.03 | 0.99 | 0.53 | 0.35 | 0.14 |
| 5 | 0.47 | 0.46 | 0.45 | 0.25 | 0.35 | 0.09 |
| 1 | 0.16 | 0.16 | 0.15 | 0.13 | 0.07 | 0.06 |
| Background | 0.10 | 0.10 | 0.10 | 0.10 | 0.07 | 0.06 |
| Background (450 nm) | 0 | 0.01 | 0.02 | 0 | 0.27 | 0.29 |

As can be seen from the table, when a nitrocellulose membrane was used as the support, the blue spot was decomposed to gray and the background was changed to yellow, so that the detection sensitivity was lowered from 0.2 ng to 2 ng after 22 hours. In contrast, when a hydrophobic polyvinylidene fluoride membrane was used, the blue spot was stable and the reflection density of the background was not raised, so that the detection sensitivity remained at 0.2 ng after 22 hours.

Although the invention was described based on the preferred embodiments thereof, it is apparent for those skilled in the art that various modifications may be made without departing the spirit and scope of the present invention.

We claim:

1. A method of assaying a target substance selected from proteins, nucleic acids, hormones, lipids, complex carbohydrates, glycolipids, polysaccharides, enzymes, vitamins, anitgens and antibodies, said method comprising the steps of:

fixing on a hydrophobic polyvinylidene fluoride membrane a complex of the target substance to be assayed and a labelled substance which specifically reacts with the target substance, said labelled substance being labelled with peroxidase;

contacting hydrogen peroxide, an aromatic primary amine compound and a phenolic compound with the peroxidase on the membrane to generate and deposit color on the hydrophobic membrane, said aromatic primary amine being a p-phenylene diamine of the formula I:

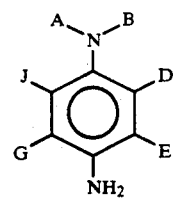

wherein A and B independently represent hydrogen or alkyl, or A and B cooperatively form a heterocyclic ring with the nitrogen; D, E, G and J independently represent hydrogen, halogen, hydroxy, amino, alkoxy, acylamide, arylsulfonamide, alkylsulfonamide or alkyl, and said phenolic compound being represented by the formula II:

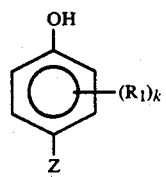

wherein $R_1$ represents an aliphatic carbohydrate residue, an alicylcic residue, a heterocyclic residue, an aryl group, —SCN, —OR$_4$, —OCOR$_4$, —OSO$_2$R$_4$, —SR$_4$,—OCONHR$_4$, —OSO$_2$NHR$_4$,

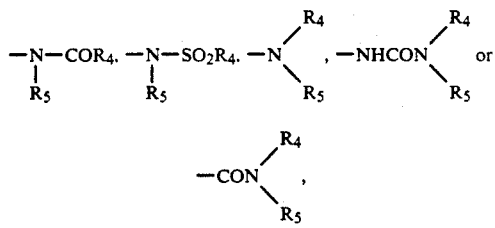

wherein $R_4$ and $R_5$ independently represent hydrogen, an aliphatic carbohydrate residue, an alicyclic residue, an aryl group or a heterocyclic residue, Z represents hydrogen, a detaching group selected from —OR$_2$, —OCOR$_2$, —OSO$_2$R$_2$, —SR$_2$,—OCONHR$_2$, —OSO$_2$NHR$_2$,

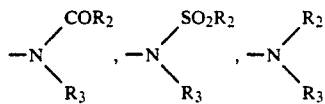

and —SCN, where $R_2$ and $R_3$ are the same or different and represent hydrogen, an aliphatic carbohydrate residue, an alicyclic residue, an aryl group or a heterocyclic residue, or a detaching halogen atom and k represents an integer of 1 to 4; and measuring the color deposited on the hydrophobic membrane.

* * * * *